United States Patent

Hsiao et al.

[11] Patent Number: 6,112,013
[45] Date of Patent: Aug. 29, 2000

[54] APPARATUS FOR DETECTING A CRACK IN A HEATER OF AN ACID AND RINSE BATH AND A METHOD OF CRACK DETECTION OF THE SAME

[75] Inventors: Tsai-fu Hsiao, Changhua; Yu-Shaw Tai, Hsinchu; Kuo Tung-Chu, Taipei, all of Taiwan

[73] Assignee: United Microelectronics Corp., Hsinchu, Taiwan

[21] Appl. No.: 09/140,775

[22] Filed: Aug. 26, 1998

[51] Int. Cl.[7] ............................................. H05B 3/40
[52] U.S. Cl. ........................ 392/497; 392/503; 392/498; 219/523
[58] Field of Search ................................ 392/497, 503, 392/498; 219/523, 437

[56] References Cited

U.S. PATENT DOCUMENTS

| | | | |
|---|---|---|---|
| 3,617,701 | 11/1971 | Volker | 392/503 |
| 4,103,319 | 7/1978 | Crain et al. | 361/106 |
| 4,234,785 | 11/1980 | Lefebvre | 219/523 |
| 5,155,800 | 10/1992 | Rezabek et al. | 392/503 |
| 5,290,516 | 3/1994 | Greco et al. | 422/57 |
| 5,503,704 | 4/1996 | Bower et al. | 156/281 |
| 5,850,503 | 12/1998 | Onken | 392/441 |

*Primary Examiner*—Teresa Walberg
*Assistant Examiner*—Shawntina Fuqua

[57] ABSTRACT

A method and an apparatus for detecting the crack of a heater of an acid and rinse bath, acid and rinse bath is filled with acid solution, a heater is used to heat the acid solution. A heater is constituted of a hollow quartz tube with one closed end and one open end, the closed end is submerged into acid solution, part of the quartz tube is exposure in the air. The heated filament is inserted into the open end of the heater through the closed end of the heater, moisture detecting device is attached on the inner side wall of the quartz tube, use chemicals that will change color by absorbing moisture, or use electronic component to detect the humidity, monitoring the variation of moisture in the quartz tube to acknowledge is there any crack of the quartz tube, and replace the defect quartz tube before too late.

14 Claims, 2 Drawing Sheets

APPARATUS FOR DETECTING A CRACK IN A HEATER OF AN ACID AND RINSE BATH AND A METHOD OF CRACK DETECTION OF THE SAME

BACKGROUND OF THE INVENTION

1. Field of the Invention

The present invention relates to heaters in an acid and rinse bath, and more specifically, to a method and an apparatus for detecting the crack of a heater in an acid and rinse bath.

2. Description of the Prior Art

There are hundreds of steps in integrated circuit manufacturing processes to the semiconductor devices on a wafer, for example, thermal oxidation process, photolithography process, etching process or cleaning process. Among others, chemical cleaning process is used very frequently in a semiconductor factory for wafer cleaning of particle, organic, and metal contamination. In general, the chemical cleaning processes use a series of cleaning steps. The chemical cleaning processes are designed for different kinds of semiconductor device pollution, especially for cleaning some contaminations such as metal silicide, refractory metal layer, aluminum, sputtered glass layer and deposited glass layer. Chemical cleaning processes for Si layer or $SiO_2$ layer are performed before proceeding with any high temperature processes such as an oxidation process, diffusion process, deposition process or annealing process.

There are several chemical cleaning processes in normal, such as stripping the residue photoresist on substrate by using plasma, then being submerged into $H_2SO_4$-$H_2O_2$ solution to clean the surface of the substrate and maintain the temperature between 18 to 23 degrees centigrade; likely, it is also possible for cleaning the surface of the substrate by deionized water(DI water), then use heated $N_2$ gas to dry. Above mentioned cleaning processes are often used in wafer fabrication.

Conventional chemical cleaning is performed with a series of acid and rinse baths. A mixture of $NH_4OH$, $H_2O_2$ and $H_2O$ is prepared in acid and rinse bath and heated to 60–80° C. The wafers are submerged in the solution for 10–15 minutes, then removed and rinsed in DI water. The usage of wafer cleaning with an acid and rinse bath can remove organism or metal contaminations on the surface of the substrate.

The temperature of the solution in the acid and rinse bath should be maintained around but not above 80° C. A heated filament is submerged in the solution in order to maintain the temperature of the solution. Normally the heated filament is inserted into a quartz tube in order to avoid the corrosive solution reaction with the filament and cause severe pollution of the wafers.

Referring to FIG. 1, a cross sectional view of an acid and rinse bath 1000 is shown. Acid solution 1100 mixed by ($NH_4OH$): $H_2O_2$: $H_2O$ in about (0.1~1): 1:5 by volume is filled into the acid and rinse bath 1000. The mix ratio of the solution depends on the different processes.

Still with reference to FIG. 1, heater 2000 is submerged into acid solution 1100 to heat the solution. The exterior shell of the heater 2000 is a hollow quartz tube 2100 with one open end and one closed end. Part of the quartz tube 2100 is submerged in acid solution 1100 with closed end thereof, another end of the quartz tube 2100 stretching out of the acid solution 1100. Heated filament 2200 is inserted into quartz tube 2100 from the open end of the quartz tube 2100 to reach to the closed end of the quartz tube 2100. The acid solution 1100 is heated by the electrically connected heated filament 2200 via quartz tube 2100.

Prolonged heating times are necessary since acid solution 1100 should always be maintained between 75 to 80° C. Since the quartz tube 2100 will be corroded by acid solution 1100, long term immersion will cause heated filament 2200 to pollute the acid solution 1100; silicon wafers will also get contaminated and must be scrapped.

Unfortunately, a crack in the quartz tube 2100 is buried in acid solution 1100 and not easy to find out during operation. Therefore, it is desirable to have a detecting device to detect a crack in the heater of an acid and rinse bath. This crack detection device shall inform the operator to change the defective parts in order to maintain good wafer yields and reduce wafers loss.

SUMMARY OF THE INVENTION

A method and an apparatus for detecting the crack of a heater of an acid and rinse bath according to the present invention is disclosed. The method includes inserting a heated filament into said heater, wherein said heater is a hollow quartz tube with one open end and one closed end. A heated filament is inserted from the open end and extends to the immersed closed end. Then, a moisture detecting device is placed within the heater, wherein said moisture detecting device is attached to the inner wall of the quartz tube. The moisture detecting device is a small tube with chemicals filled inside, in which the chemicals will change color when water gets in the tube. The chemicals are selected from the group consisting of anhydride cupric sulfate, cobalt chloride and the combinations thereof. The moisture detecting device may also be an electronic component which can monitor the humidity inside the quartz tube. The heater is then mounted in the acid solution of the bath with part of the heater inside the acid solution and the other part out of the acid solution, in which the acid solution is a mixture of $NH_4OH$, $H_2O_2$ and $H_2O$. The acid solution is heated by the heated filament, and the moisture detecting device is used to detect the incoming moisture in the quartz tube to provide an indication whether or not there is any crack in the hollow quartz tube.

BRIEF DESCRIPTION OF THE DRAWINGS

The foregoing aspects and many of the attendant advantages of this invention will become more readily appreciated as the same becomes better understood by reference to the following detailed description, when taken in conjunction with the accompanying drawings, wherein.

DESCRIPTION OF THE PREFERRED EMBODIMENT

A method and an apparatus for detecting a crack of a heater of an acid and rinse bath is disclosed. A moisture detecting device, for example, chemicals is provided that will change color when react with moisture, or electronic moisture detecting device is used to detect the moisture in the quartz tube, mounted on the inner side wall of hollow quartz tube. When some moisture gets into the quartz tube via the crack, the moisture detecting device will acknowledge this situation.

Figure 1:
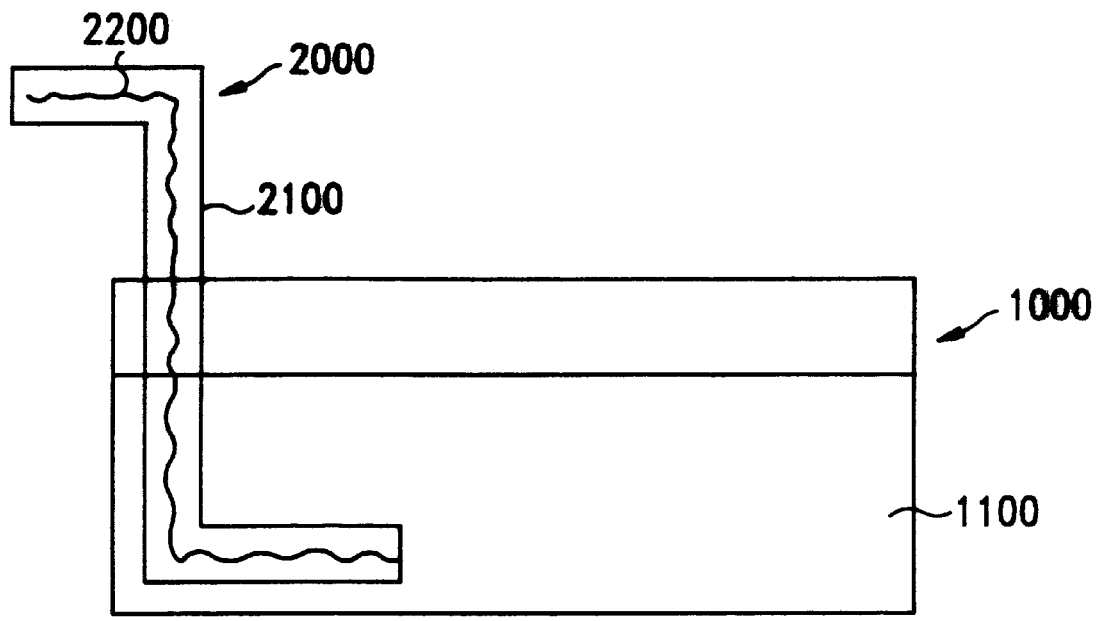
FIG. 1 is a cross sectional view of an acid and rinse bath and a heater, illustrating the heater submerged into the acid and rinse bath in accordance with prior art.
Figure 2:
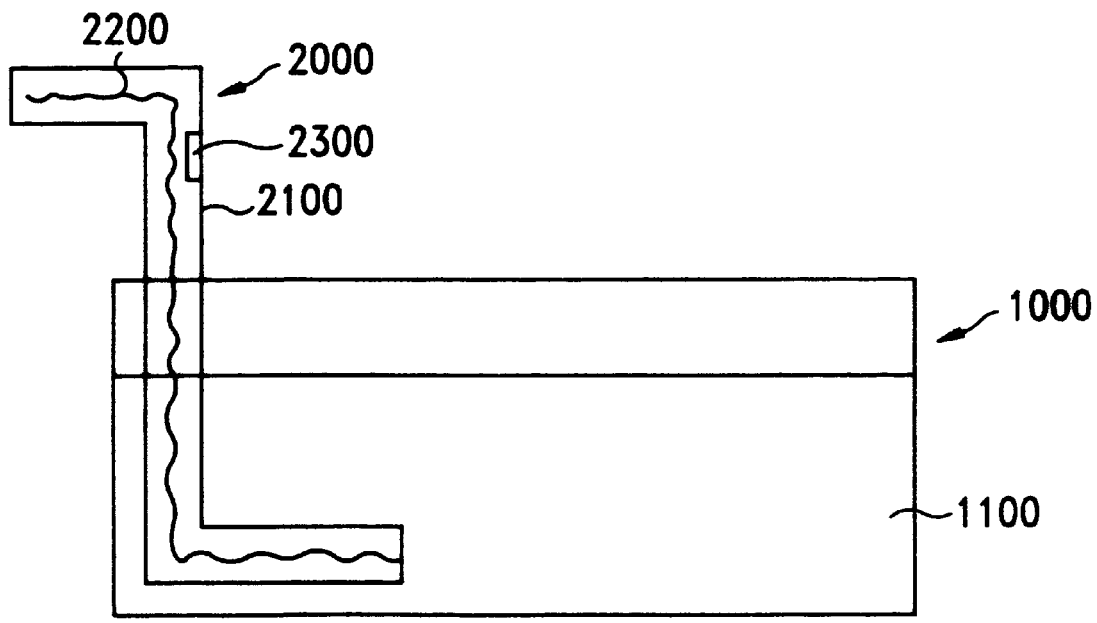
FIG. 2 is a cross sectional view of an acid and rinse bath and a heater with moisture detecting device, illustrating the method to detect whether there is any incoming moisture in the heater or not, in order to judge the crack of the side wall of the heater in accordance with present invention.

Referring to FIG. 2, it shows a cross sectional view of an acid and rinse bath 1000 and a heater 2000 is depicted. Acid solution 1100 mixed by $H_2O$, $NH_4OH$ and $H_2O_2$ in about 5:(0.1~1):1 by volume is filled into the acid and rinse bath 1000, in which the mix ratio depends on the different processes. Acid solution 1100 have to maintained at 60–80° C. for the purpose of cleaning.

Acid solution 1100 is heated by a heater 2000 which includes of a hollow quartz tube 2100 with one closed end and one open end. The closed end of quartz tube 2100 is submerged into acid solution 1100 with the other open end in contact with air. Heated filament 2200 is a heating element inside the heater 2000 that is inserted from the open end of quartz tube 2100 to the closed end of quartz tube 2100. Electric power is used to heat the bath during operation.

Further referring to FIG. 2, the heater 2000 has three quartz tube sections 2100 which are joined in rectangular form and half of quartz tube 2100 is immersed into the acid solution. Although the preferred embodiment is made of three quartz sections 2100, there is no limit to the shape of the quartz tube 2100, but rather various modifications and arrangements can also be used in the present invention to detect the crack of quartz tube 2100.

Referring to FIG. 2, there is attached a moisture detecting device 2300 at the inner side wall of quartz tube 2100 of heater 2000. Moisture detecting device 2300 can use chemicals, for example, anhydride cupric sulfate and cobalt chloride, that will absorb moisture and change their color therefrom, which are filled in capillary tube as moisture detecting device 2300.

When chemicals serve as moisture detecting device 2300, the color difference of chemicals has to be visually checked to ensure that there is no incoming moisture in the quartz tube 2100 and the tube will be replaced while chemicals change its color. The position of the moisture detecting device 2300 is very important according to above description and should be easy to be checked by the operator, for example, at the inner side walls of quartz tube 2100 above the level of acid solution 1100.

Figure 3:
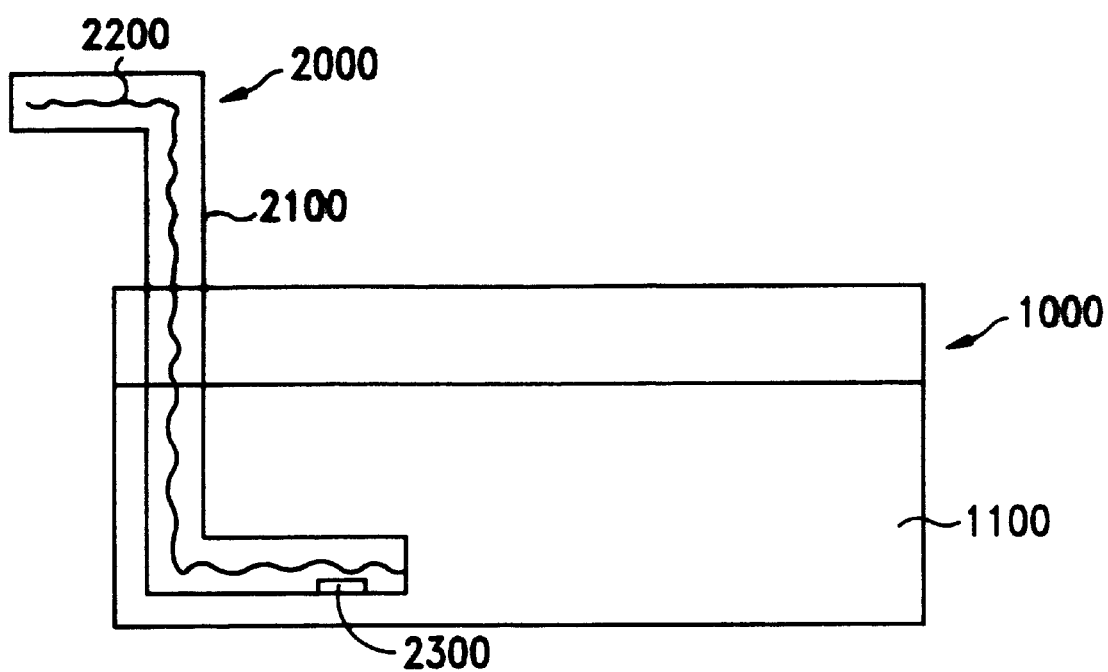
FIG. 3 is a cross sectional view of an acid and rinse bath and a heater with electronic moisture detecting device mounted at the bottom of the heater to more readily to detect the moisture in the heater.

Referring to FIG. 3, now it shows a cross sectional view of acid and rinse bath 1000 and heater 2000, with the structure of acid and rinse bath 1000 and heater 2000 similar to FIG. 2 but the position of moisture detecting device 2300 is different from FIG. 2 since an electronic component is utilized to detect the humidity. It's not necessary to locate the moisture detecting device 2300 above the level of said solution 1100.

Referring to FIG. 3, the moisture detecting device 2300 is also attached to the inner side walls of the quartz tube 2100 but under the level of acid solution 1100. It is not necessary to use vision to check the moisture detecting device 2300 because of the use of electronic component. For better detection of this moisture detecting device 2300, it is possible to mount it near the closed end of quartz tube 2100 or under the level of acid solution 1100. It is easier to detect the crack of the quartz tube 2100 since the cracks always happens under the level of acid solution 1100.

According to above mentioned description, a moisture detecting device is installed at the inner side walls of a quartz tube to detect or monitor the incoming moisture due to the crack of quartz tube. Replacement of the tube when cracks are detected will prevent the heated filament from polluting the acid solution.

As is understood by a person skilled in the art, the foregoing preferred embodiments of the present invention are illustrated of the present invention rather than limiting of the present invention. It is intended to cover various modifications and similar arrangements included within the spirit and scope of the appended claims, the scope of which should be accorded with the broadest interpretation so as to encompass all such modifications and similar structure.

What is claimed is:

1. A method of detecting a crack of a heater in an acid and rinse bath, said method comprising:

inserting a heated filament into a heater, wherein said heater is a hollow quartz tube with both ends, said heated filament being inserted into said quartz tube from one end towards the other end;

mounting only one connection-free moisture detector into said heater, wherein said moisture detector is attached to an inner side wall of said hollow quartz tube independently, and color of said moisture detector changes responding to moisture being detected;

submerging part of said heater into an acid solution of said acid and rinse bath, part of said heater stretching out of said acid solution;

heating said acid solution by using said heated filament; and using said moisture detector to detect the incoming humidity in said hollow quartz tube to acknowledge whether or not there is said crack in said hollow quartz tube.

2. The method of claim 1, wherein said acid solution is a mixture of $NH_4OH$, $H_2O_2$ and $H_2O$.

3. The method of claim 1, wherein said heater includes said quartz tube with a closed end and an open end, said closed end of said quartz tube being submerged into said solution, and said open end of said heater being used to insert said heated filament and reach to said closed end, so that said quartz tube encompasses said heated filament.

4. The apparatus of claim 1, wherein said moisture detector is a tube with chemicals inside for detecting incoming moisture in said heater.

5. The method of claim 4, wherein said chemicals are selected from the group consisting of anhydride cupric sulfate and cobalt chloride.

6. An apparatus for detecting a crack of a heater in an acid and rinse bath, said apparatus comprising:

a heated filament mounted in said heater, said acid and rinse bath being filled with an acid solution, said heater being used to heat said acid solution, and said heater being a hollow quartz tube with two ends, said heated filament being inserted from one end to the other end of said quartz tube, part of said heater being submerged in said acid solution, and part of said heater stretching out of said acid solution; and a single connection-free moisture detector attached on an inner side wall of said quartz tube independently for detecting the incoming moisture in said hollow quartz tube of said heater, and color of said moisture detector changes responding to moisture been detected.

7. The apparatus of claim 6, wherein said acid solution is a mixture of $NH_4OH$, $H_2O_2$ and $H_2O$.

8. The method of claim 6, wherein said heater includes said quartz tube with a closed end, said closed end of said heater being submerged into said acid and rinse bath, another end of said heater being used for insertion of said heated filament, so that said heated filament is encompassed by said quartz tube.

9. The apparatus of claim 6, wherein said moisture detector is a tube with chemicals inside for detecting incoming moisture in said heater.

10. The apparatus of claim 9, wherein said chemicals are selected from the group consisting of anhydride cupric sulfate and cobalt chloride.

11. An apparatus for detecting a crack of a heater in an acid and rinse bath, the apparatus comprising:

a heated filament mounted in said heater for heating an acid solution, said acid and rinse bath being filled with the acid solution, part of said heater being submerged in said acid solution, and part of said heater stretching out of said acid solution, said heater including a quartz tube with a closed end and an open end, said closed end of said heater being submerged in the acid and rinse bath, said open end is used to insert said heated filament, so that said heated filament is encompassed by said quartz tube, said heated filament is located in said quartz tube from said open end to said closed end; and a single connection-free moisture detector being attached on the inner side wall of said quartz tube independently for detecting the incoming moisture in said hollow quartz tube of said heater, wherein the color of said moisture detector changes responding to moisture being detected.

12. The apparatus of claim 11, wherein said acid solution is a mixture of $NH_4OH$, $H_2O_2$ and $H_2O$.

13. The apparatus of claim 11, wherein said moisture detector is a tube with chemicals inside for detecting incoming moisture in said heater.

14. The apparatus of claim 13, wherein said chemicals are selected from the group consisting of anhydride cupric sulfate and cobalt chloride.

* * * * *